(12) United States Patent
Passmore (10) Patent No.: US 10,010,254 B2
(45) Date of Patent: Jul. 3, 2018

(54) SURFACE MOUNTABLE SENSOR ARRAY FABRIC

(71) Applicant: WAVE ARRAY SCIENCE, INC., Wichita, KS (US)

(72) Inventor: Charles Gregory Passmore, Austin, TX (US)

(73) Assignee: WAVE ARRAY SCIENCE, INC., Wichita, KS (US)

( * ) Notice: Subject to any disclaimer, the term of this patent is extended or adjusted under 35 U.S.C. 154(b) by 421 days.

(21) Appl. No.: 14/868,124

(22) Filed: Sep. 28, 2015

(65) Prior Publication Data

US 2017/0086681 A1    Mar. 30, 2017

(51) Int. Cl.
*A61B 8/00* (2006.01)
*A61B 5/026* (2006.01)
*A61B 5/00* (2006.01)
*A61B 7/00* (2006.01)
*A61B 8/08* (2006.01)
*A61B 8/13* (2006.01)

(52) U.S. Cl.
CPC ............ *A61B 5/026* (2013.01); *A61B 5/0004* (2013.01); *A61B 5/489* (2013.01); *A61B 5/6825* (2013.01); *A61B 5/6833* (2013.01); *A61B 5/7225* (2013.01); *A61B 7/00* (2013.01); *A61B 8/00* (2013.01); *A61B 5/6801* (2013.01); *A61B 5/742* (2013.01); *A61B 8/08* (2013.01); *A61B 8/13* (2013.01); *A61B 8/4281* (2013.01); *A61B 8/483* (2013.01); *A61B 2562/046* (2013.01)

(58) Field of Classification Search
CPC ....... A61B 5/026; A61B 5/0004; A61B 5/742; A61B 5/7225; A61B 5/6801; A61B 5/6833; A61B 5/489; A61B 5/6825; A61B 7/00; A61B 2562/046; A61B 8/00; A61B 8/08; A61B 8/13; A61B 8/4281; A61B 8/483

See application file for complete search history.

(56) References Cited

U.S. PATENT DOCUMENTS

2005/0020918 A1*  1/2005  Wilk .................... A61B 5/6804
                                                          600/439
2010/0234714 A1*  9/2010  Mercier ............ A61B 5/02438
                                                          600/388

\* cited by examiner

*Primary Examiner* — Elmer Chao
(74) *Attorney, Agent, or Firm* — ARC IP Law, PC; Joseph J. Mayo (57) ABSTRACT

A fabric with an integrated sensor array and optionally with an integrated display; the fabric may be mounted to the surface of an object to be measured or monitored. The fabric may comprise multiple laminar layers, such as sensor layers, processing layers, display layers, and cladding layers for protection and sealing. Data analysis performed by processing layers may include beamforming operations, frequency filters, or any desired transformations. An illustrative display uses a layer of liquid crystal cells sandwiched between polarizing filter layers. An illustrative sensor array is an array of piezoelectric acoustic sensors formed by adjacent layers of calcium carbonate cells and potassium bitartrate cells. An application of acoustic sensor arrays may include for example a patch attached to a person's skin that senses and displays the location and size of blood vessels under the skin using the sound generated by blood flow.

17 Claims, 10 Drawing Sheets

SURFACE MOUNTABLE SENSOR ARRAY FABRIC

BACKGROUND OF THE INVENTION

Field of the Invention

One or more embodiments of the invention are related to the field of measuring instruments. More particularly, but not by way of limitation, one or more embodiments of the invention enable a sensor array integrated into a fabric that may be attached to or placed near an object to be measured. The fabric may include integrated data analysis capabilities and an integrated display.

Description of the Related Art

Sensor arrays are known in the art. For example, phased array radar systems are in widespread use. Microphone arrays for reception and processing of acoustic signals are also known. An array of sensors provides several potential advantages over individual sensors, including for example improved directionality of signal reception. These radar and microphone arrays are typically large, expensive instruments that are installed into a site or an area.

Sensors that can be attached to a surface of an object are also known in the art. For example, relatively low-cost, wearable sensing devices exist for selected applications. These devices generally contain individual sensors, such as motion sensors or heartbeat sensors. They are often designed as rigid components that are attached to a user for example using a wristband.

Combining the technological advantages of sensor arrays with the convenience and cost efficiency of surface mountable or wearable devices offers several potential benefits. There are no known devices that provide these solutions.

For at least the limitations described above there is a need for a surface mountable sensor array fabric.

BRIEF SUMMARY OF THE INVENTION

One or more embodiments described in the specification are related to a surface mountable sensor array fabric. Embodiments of the system measure one or more properties of an object using a sensor array embedded into a fabric that is attached to or placed near the object.

One or more embodiments of the system include a fabric that can be mounted to or placed near or in proximity to a surface of an object to be measured. The fabric may comprise a sheet of material that may contain one or more laminar layers. The bottom side of the sheet may be attached to or placed near the surface of the object to be measured; the top side of the sheet may be visible to a viewer looking at the mounted sheet. Various components of the system may be integrated into one or more of the layers. One or more layers may contain a sensor array, which comprises sensors of any type, configured to measure any property or properties of the object. One or more layers may contain a communications array with electrical connections to the sensors of the sensor array. The communications array may read sensor data from each sensor in the array; in one or more embodiments it may also provide power or control signals to the sensors in the sensor array. Sensor data may be transferred to a sensor data analysis subsystem that comprises one or more processors. These processors may be external to the sheet, or integrated into one or more layers of the sheet. The sensor data analysis subsystem may generate one or more outputs using any analysis or data transformation techniques; these outputs may be transferred to a display subsystem comprising one or more displays. The displays may be external to the sheet, or integrated into one or more layers of the sheet.

One or more embodiments may include a display integrated into one or more layers and visible to a viewer that looks at the top side of the sheet. For example, an integrated display may be a liquid crystal display with a layer of liquid crystal cells that form pixels of the display. One or more embodiments may include additional display layers such as power, control, and communication lines; light polarizers; and reflective, transmissive, or transflective layers.

Sensor arrays in embodiments may measure any property or set of properties in any region or regions of the object. In one or more embodiments sensor arrays are configured to measure a grid of object regions, for example by associating a subset of the array with each region of the object. These configurations may for example provide a map of a property across the object. For example, sensor array elements may be partitioned into subarrays that each measure a region of the object located below or near the subarray when the sheet is placed on or near the object. In embodiments with an integrated display layer, the display may show the object property or an output derived from this property for the region of the object directly below or near each pixel or region of the display. This configuration in a sense effectively allows a viewer to look through the surface of the object to observe the object's underlying properties. As an illustrative example, one or more embodiments may have an array of temperature sensors, and a corresponding array of display pixels in a display layer. The fabric may then provide a temperature map for the surface of the object (or for regions below the surface), where the output on the display (such as a color for example) corresponds to the temperature of the object directly below that portion of the display.

One or more embodiments may use one or more processors for sensor data analysis. These processors may be integrated into one or more layers of the sheet, or they may be external to the sheet. In one or more embodiments there may be both integrated processors in one or more layers and external processors. One or more embodiments may use any type or types of processors, including for example, without limitation, a microprocessor, an array of microprocessors, a digital signal processor, an array of digital signal processors, an analog filter circuit, an array of analog filter circuits, a computer, a laptop computer, a tablet computer, a desktop computer, a server computer, a network of computers, a mobile device, and a network of mobile devices.

In one or more embodiments a sensor data analysis subsystem may use any technique or techniques to analyze sensor data and to create one or more outputs for display or for further analysis. For example, without limitation, data analysis may include application of beamforming signal processing methods to sensor data. Beamforming may be used for example to amplify signals arriving from one set of directions and to attenuate signals arriving from another set of directions. Data analysis may also include for example, without limitation, application of one or more of a band-pass filter, a band-stop filter, a high-pass filter, or a low-pass filter to sensor data or to the output of other analysis stages.

One or more embodiments may have a large number of sensors in a sensor array, for example 100 sensors, 1000 sensors, or more. One or more embodiments may have a high density of sensors per square centimeter of surface area of the sheet, for example 10 sensors per square centimeter, 1000 sensors per square centimeter, or more. For example, 3D printing technology may be used to create one or more embodiments with small sensor cells and high-density sensor arrays.

Embodiments may have sensor arrays with any type or types of sensors. One or more embodiments include acoustic sensors, which may be for example, without limitation, piezoelectric acoustic sensors. One or more embodiments may generate piezoelectric acoustic sensors from two adjacent layers, one of which contains cells of calcium carbonate, and the other of which contains corresponding cells of potassium bitartrate.

One or more embodiments may have an inner cladding layer located on the bottom side of the sheet, which is adjacent to the surface of the object to be measured. One or more embodiments may have an outer cladding layer located on the top side of the sheet. Cladding layers may for example protect components of the sheet from the environment. An inner cladding layer may provide material that attaches to or interfaces with the object to be measured.

In one or more embodiments the sheet may be configured to be attached to or placed near a person, and the sensor array may measure one more biological properties of one or more body parts. Biological properties measured may include for example, without limitation, sound, pressure, temperature, sweat rate, electric resistance, electric conductivity, electrical voltage, electrical current, electromagnetic field, motion, orientation, fluid flow, strain, pH, tissue type, tissue composition, cell type, and chemical composition.

One or more embodiments may include acoustic sensors that measure the sound of blood flow. These sounds may be used for example to measure the presence or size of blood vessels beneath the sheet. An integrated display may be included to show the blood vessels directly on the sheet. A potential application for a blood vessel detecting sheet is phlebotomy, where the attached sheet allows a clinician to visualize blood vessels beneath the skin.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A surface mountable sensor array fabric will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
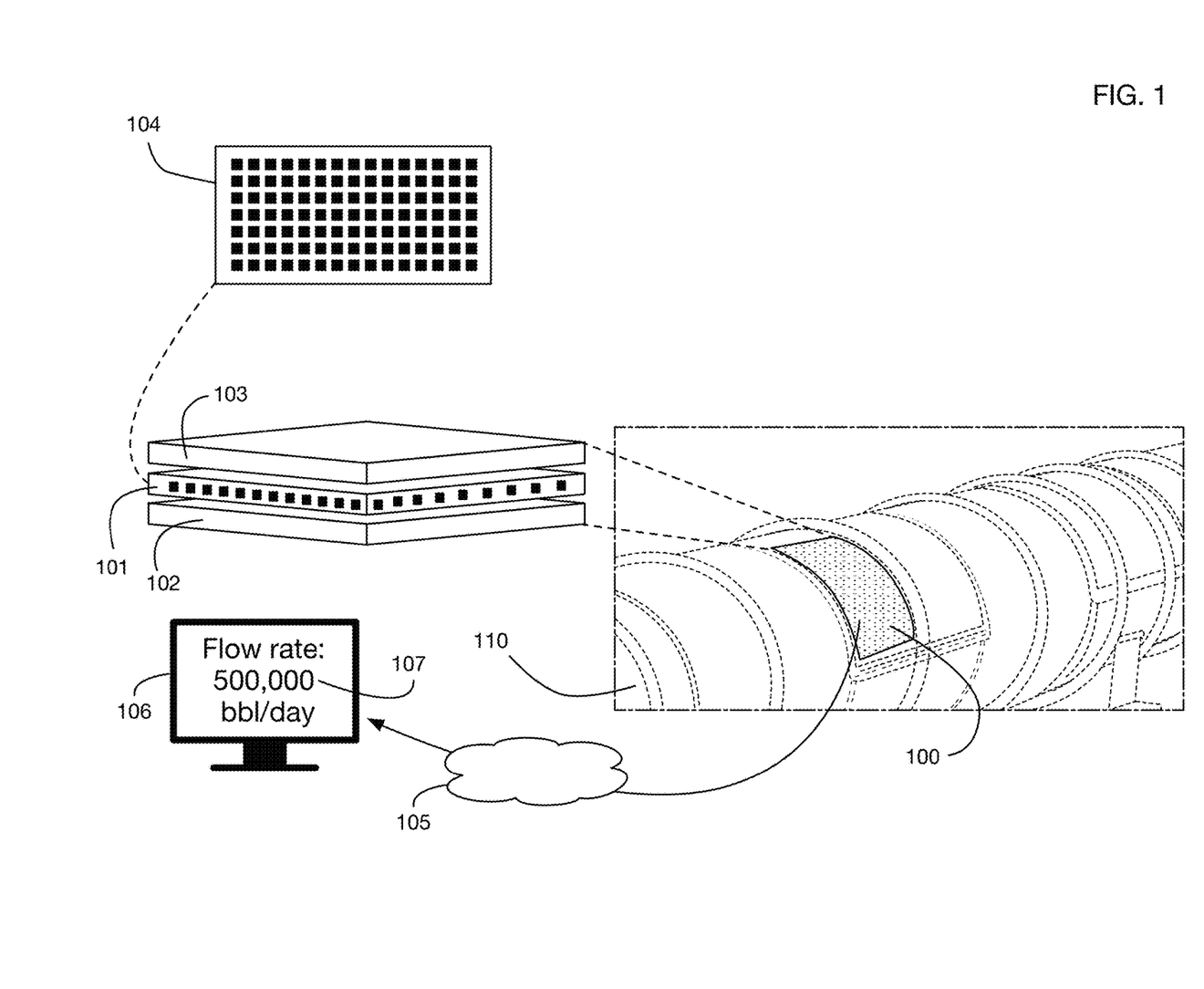
FIG. 1 illustrates an an embodiment of the invention that embeds a sensor array into a patch placed on a pipeline; the sensor array measures and reports the flow rate through the pipeline.

FIG. 1 shows an illustrative embodiment of the invention configured to be placed on the surface of a pipeline 110. One or more embodiments of the invention may be configured to be placed on, near, or in the vicinity of a surface or surfaces of any type of object or objects to be measured. This embodiment comprises a fabric 100 with at least three layers: sensor array layer 101, inner cladding layer 102, and outer cladding layer 103. These layers are illustrative; one or more embodiments may comprise a fabric with any number of layers comprising any number and types of components in each layer. Fabric layers may be made of any material or materials. For example, in one or more embodiments some of the fabric layers may be cotton or other wearable materials. In one or more embodiments a sensor array may comprise multiple layers. In one or more embodiments there may be multiple inner cladding layers or multiple outer cladding layers. One or more embodiments may not have an inner cladding layer. One or more embodiments may not have an outer cladding layer.

Cladding materials for inner or outer cladding layers may be for example chosen to protect inner layers from the environment. Inner cladding layers may be selected for example to attach the fabric to the object being measured, such as pipeline 110 of FIG. 1. Outer cladding layers may be selected to be transparent in one or more embodiments, for example to show inner layers or elements such as an integrated display. One or more embodiments may use any type of material or materials of any size, shape, thickness, or consistency for cladding layers.

Layer 101 of the fabric shown in FIG. 1 contains a sensor array 104. This sensor array comprises a grid of sensors, configured in any desired shape or pattern. The regular rectangular grid illustrated in FIG. 1 for sensor array 104 is illustrative; one or more embodiments may use sensor arrays in any geometric pattern, including for example, without limitation, linear, polygonal, circular, elliptical, random, polar, or tiled in any periodic or non-periodic tiling pattern. One or more embodiments may arrange sensors into a non-orthogonal array, such as for example a polar array. A polar array may for example position sensors at grid points that have r and θ polar coordinates spaced at regular intervals or in any desired sequence. One or more embodiments may use a polar array, or any other non-orthogonal array, for example in order to minimize aliasing artifacts or phasing anomalies. One or more embodiments may arrange sensors into concentric circles, with any desired radial spacing between the circles and any desired angular spacing between sensors on the same circle. One or more embodiments may arrange sensors into an irregular pattern, for example with random offsets from a grid, in order to minimize aliasing artifacts or phasing anomalies. One or more embodiments may combine non-orthogonal arrays (such as polar arrays for example) with random offsets. One or more embodiments may have sensor arrays in three-dimensional patterns where the sensors in the array do not all lie on the same plane or the same surface. Sensors in a sensor array may be of any size, shape, or type. A sensor array may have any number of sensors. Sensors may measure any property or properties of an object, including for example, without limitation, position, orientation, motion, rotation, sound, vibration, temperature, charge, voltage, current, flow, chemical composition, chemical reaction, mass, weight, force, tension, stress, strain, luminance, color, density, viscosity, pressure, or electromagnetic field. One or more embodiments may have multiple types of sensors that measure different properties of an object, or that measure a single property using different modalities.

In the embodiment shown in FIG. 1, data is transmitted from fabric 100 over network 105 to computer 106, which processes the sensor data and displays output 107. One or more embodiments may transmit data over any wired or wireless network or connection. One or more embodiments may process sensor data using any algorithms or techniques to generate one or more outputs. The output 107 shows a flow rate. This output is illustrative; one or more embodiments may generate any output or outputs from sensor data. In the embodiment of FIG. 1, sensor data processing and output display are external to the fabric 100. In one or more embodiments one or more of these functions are integrated into the fabric.

Figure 2:
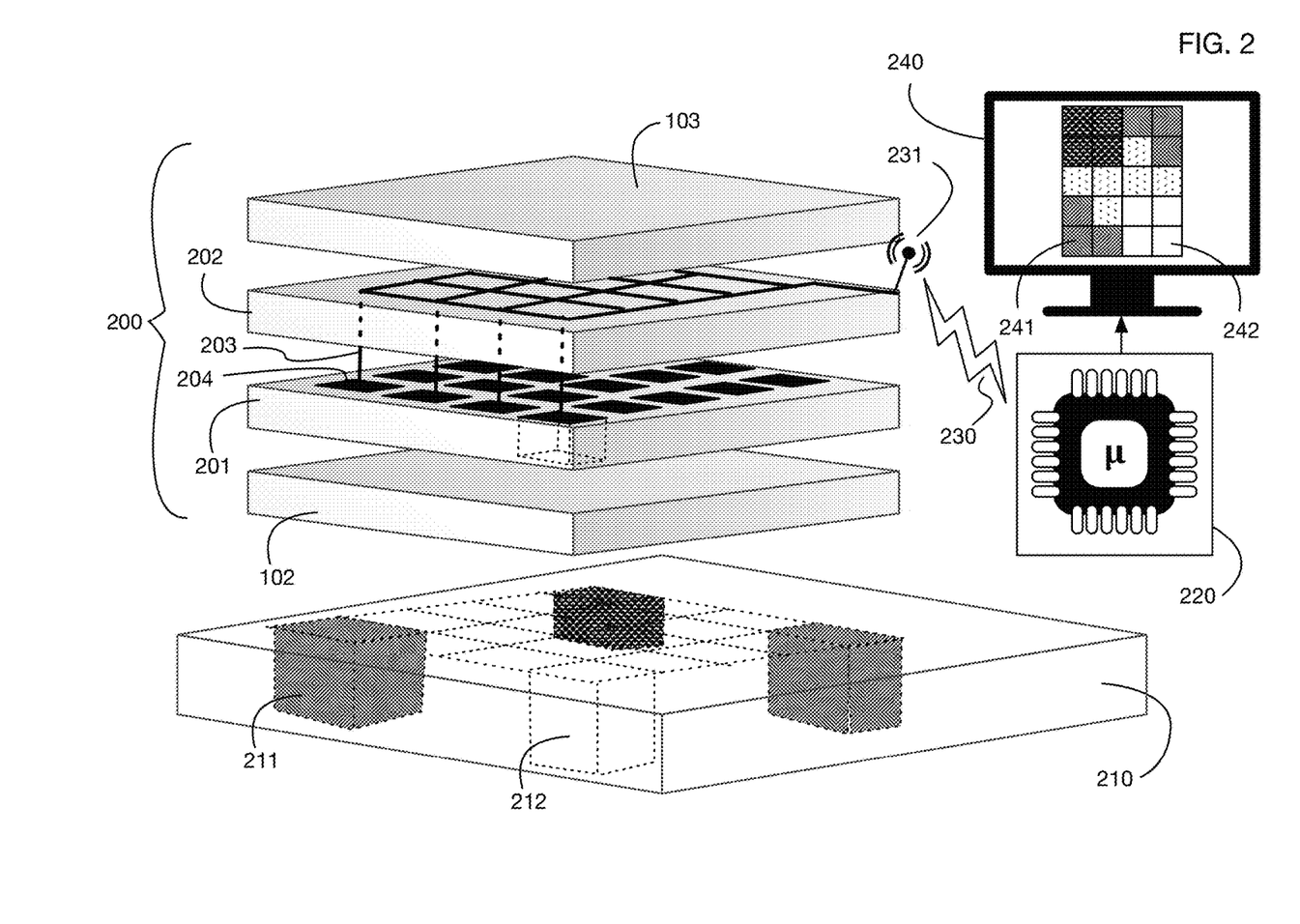
FIG. 2 illustrates an embodiment of the invention with a sensor array integrated into the fabric, and with processing and display elements external to the fabric.

FIG. 2 shows an exploded block diagram of an embodiment of the invention. Fabric 200 is configured to measure object 210. In this illustrative embodiment, fabric 200 comprises four layers, shown in an exploded view in FIG. 2. The thickness shown for the layers is for ease of illustration only; one or more embodiments may comprise layers that are arbitrarily thin, with thickness much smaller than their surface areas, for example. The bottom surface of 200 is the surface that is adjacent to or attached to object 210; inner cladding layer 102 lies along this bottom surface. The top surface of 200 is the surface opposite the bottom surface; outer cladding 103 lies along this top surface. Layer 201 comprises an array of sensors. Layer 202 comprises a communications network of electric connections to these sensors. For example, connection 203 in the network of layer 202 connects to sensor 204 in sensor array layer 201. One or more embodiments may employ one or more layers to supply power to sensors, to supply control signals to sensors, or to read data from sensors. One or more embodiments may use wireless connections to sensors instead of or in addition to wired connections to sensors. One or more embodiments may use connections between sensors to consolidate data from the sensor array in a smaller number of hub sensors, and then communicate between these hub sensors and other layers.

The connection network of layer 202 reads data from the sensor array (in addition to possibly providing power and control signals), and transmits this data to processor 220 for analysis. In the embodiment shown in FIG. 2, processor 220 is external to fabric 200. This configuration is illustrative; one or more embodiments may include one or more processors in the fabric, for example in one or more processing layers. Processor 220 may be for example, without limitation, a microprocessor, a microcontroller, a computer, a laptop computer, a notebook computer, a tablet computer, a desktop computer, a server computer, a mobile device, a digital signal processor, an analog signal processor, or any combination of the above. Processor 220 may be a network or array of processors, connected via any wired or wireless connections. In the embodiment of FIG. 2, sensor data is sent from the connection network 202 to processor 220 over wireless connection 230 by antenna 231; the antenna may for example be integrated into the connection layer 202 or into any other layer. In one or more embodiments data may be transmitted from the fabric 200 to processor 220 via a wired connection or via any combination of wired and wireless connections. Processor 220 analyzes the sensor data from sensor array 201 and generates one or more outputs. These outputs are transmitted to display 240. In the embodiment of FIG. 2, display 240 is external to fabric 200; in one or more embodiments the display may be included in the fabric for example as one or more layers.

In the embodiment of FIG. 2, each sensor in sensor array 201 is configured to measure a property of a region of object 210. For example, sensor 204 measures a property of region 211 in object 210. The value of the property is illustrated in FIG. 2 as the shading of the region; it may for example correspond to the temperature, pressure, or vibration in that region, or to any other property. In this example, the region of the object measured by the sensor is the region of the object adjacent to the sensor. This is illustrative; in one or more embodiments any sensor may measure any region or regions of any objects. The outputs displayed on display 240 correspond to the properties measured for the corresponding regions of the object. For example, pixel 241 in the display shows the measured property of region 211 of the object, and pixel 242 shows the measured property of region 212 of the object. In this configuration the outputs and the display pixels provide a map of the measured property across the object. In one or more embodiments, data from multiple sensors may be combined into a smaller number of outputs, or even into a single output as for example illustrated in FIG. 1.

Figure 3:
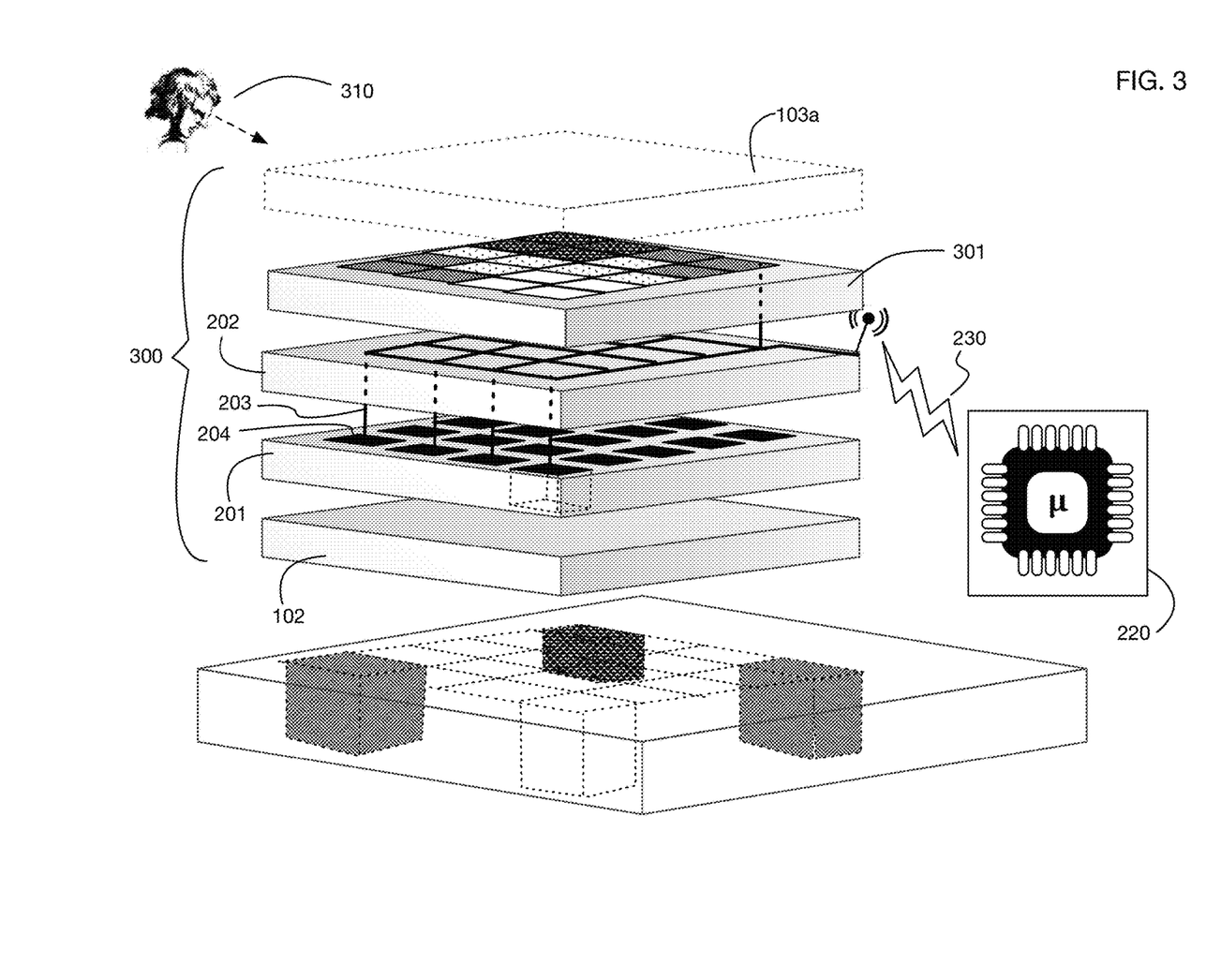
FIG. 3 illustrates an embodiment of the invention with a display integrated into the fabric.

FIG. 3 illustrates an embodiment of the invention in which the display is integrated into the fabric. Fabric 300 contains layers 102, 201, and 202 as in FIG. 2. It also contains display layer or layers 301, which integrate pixels displaying outputs from processor 220 into the fabric. In this embodiment processor 220 is external to the fabric; thus wireless link 230 may send sensor data to processor 220, which analyzes the data and sends outputs back to the display 301 over the same wireless link. The embodiment illustrated in FIG. 3 uses connection and communication network layer 202 for both reading sensor data and for writing outputs to the display layer. One or more embodiments may use separate connection and communication layers for sensors and for displays. Outer cladding layer 103a may for example be transparent so that viewer 310 can view display layer 301 when looking at the top surface of fabric 300. One or more embodiments may use an integrated display layer or layers using any display technology. Display technologies may include for example, without limitation, liquid crystals, LEDs, OLEDs, Bragg cells, electrostatic displays, thermoluminescent displays, and thermochromic displays. Integrated display layers may use any number and arrangement of pixels. Integrated displays may be for example color displays, black and white displays, or grayscale displays.

Figure 4:
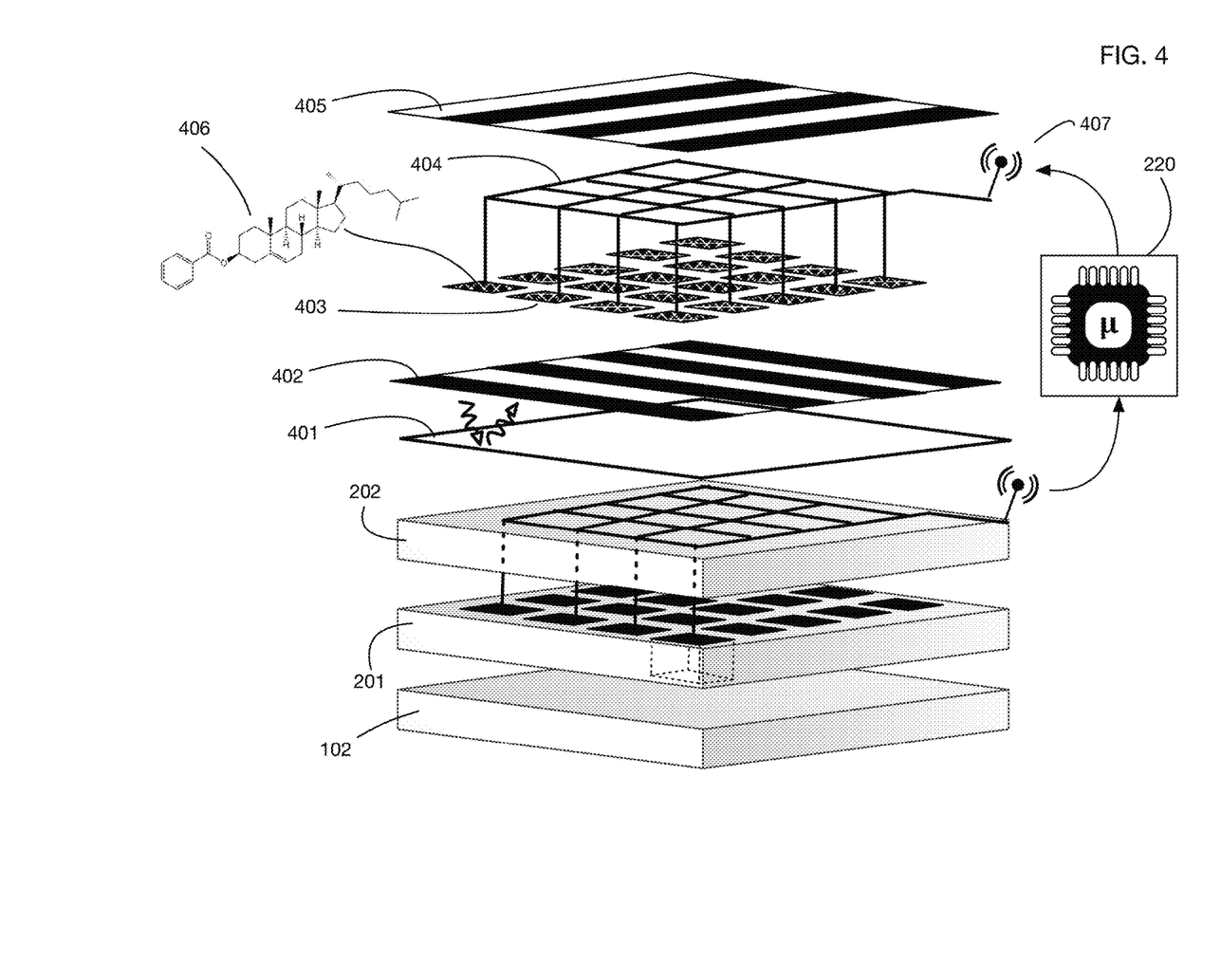
FIG. 4 illustrates an embodiment of an integrated display that uses a liquid crystal display constructed from multiple layers of the fabric.

One or more embodiments may use liquid crystal displays integrated into the fabric. FIG. 4 illustrates an exploded view of an embodiment with several layers that form a liquid crystal display. This configuration is illustrative; one or more embodiments may use any layer or layers to generate a liquid crystal display or a display using any other technology. The bottom display layer is a reflective layer 401 that reflects incoming light. This illustrative example uses a reflective LCD display; one or more embodiments may use transmissive or transflective LCD. The liquid crystal cells and the signaling lines to these cells are sandwiched between polarizing layers 402 and 405. Layer 403 contains an array of liquid crystal cells, each corresponding to a pixel of the display. As an illustration, the chemical composition 406 of the liquid crystal cells may for example contain cholesteryl benzoate ($C_{34}H_{50}O_2$). One or more embodiments may use any chemical or chemicals that generate a liquid crystal. Layer 404 contains signaling lines to control the liquid crystal cells. In the embodiment of FIG. 4, the processor 220 is external to the fabric; thus the signaling layer 404 receives output data from the processor 220 via input 407, which may be for example a wireless antenna, or a wired connection.

Figure 5:
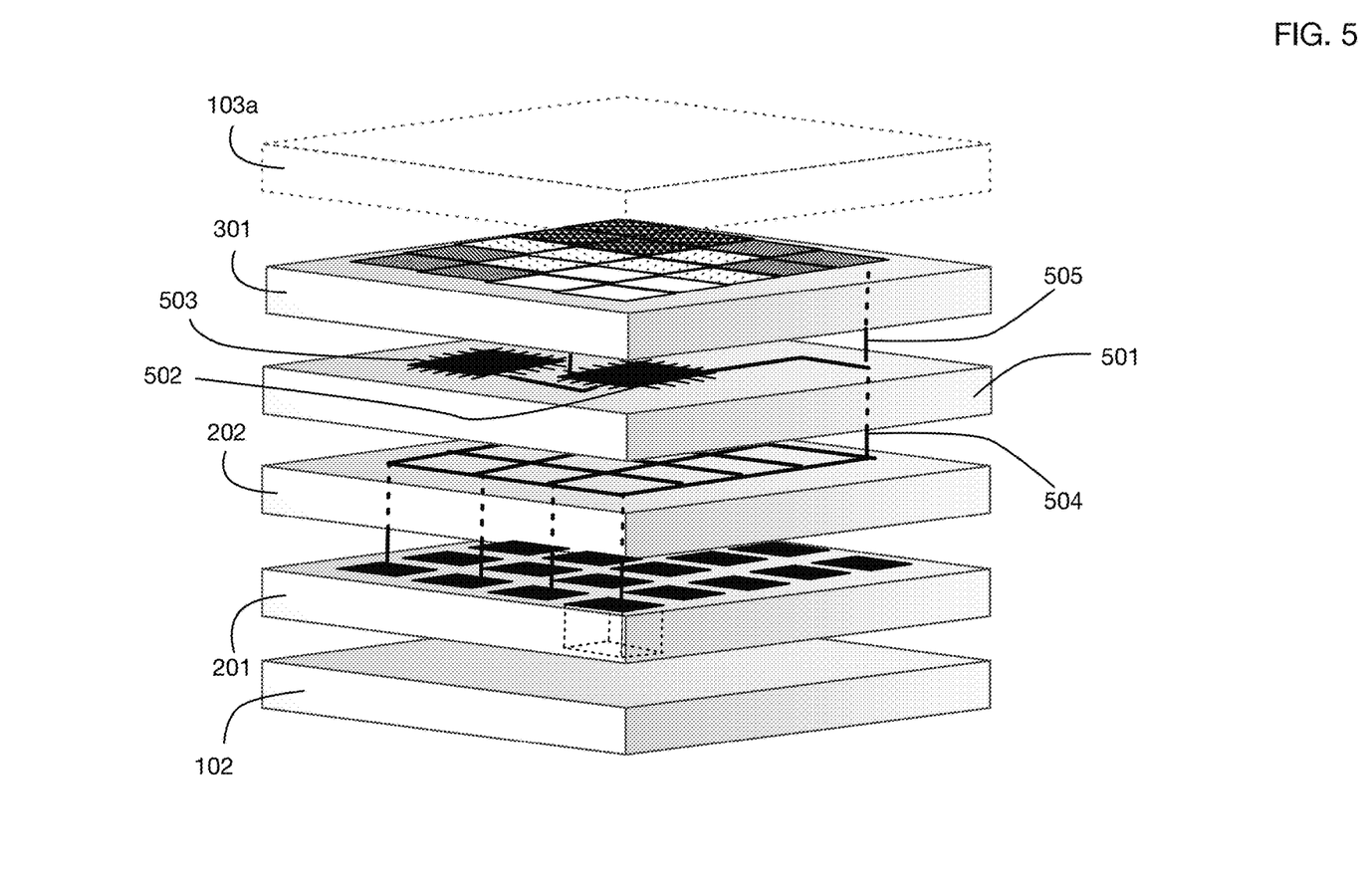
FIG. 5 illustrates an embodiment of the invention with data processors integrated into the fabric.

In one or more embodiments the fabric may contain one or more layers that include a processor or processors that analyze sensor data and generate outputs for display. FIG. 5 illustrates an embodiment with a processor layer 501. For illustration, this layer contains two microprocessors, 502 and 503. One or more embodiments may include any number of processors of any type in one or more layers. The processor layer has connections such as 504 to the layer 202 that reads sensor data from the sensor array layer 201, and connections such as 505 to the display layers. The embodiment illustrated in FIG. 5 is completely self-contained; no external processor or display is required. One or more embodiments may provide self-contained fabrics that also support transfer of data from the fabric to other components such as an external display or an external processor for further analysis.

Figure 6:
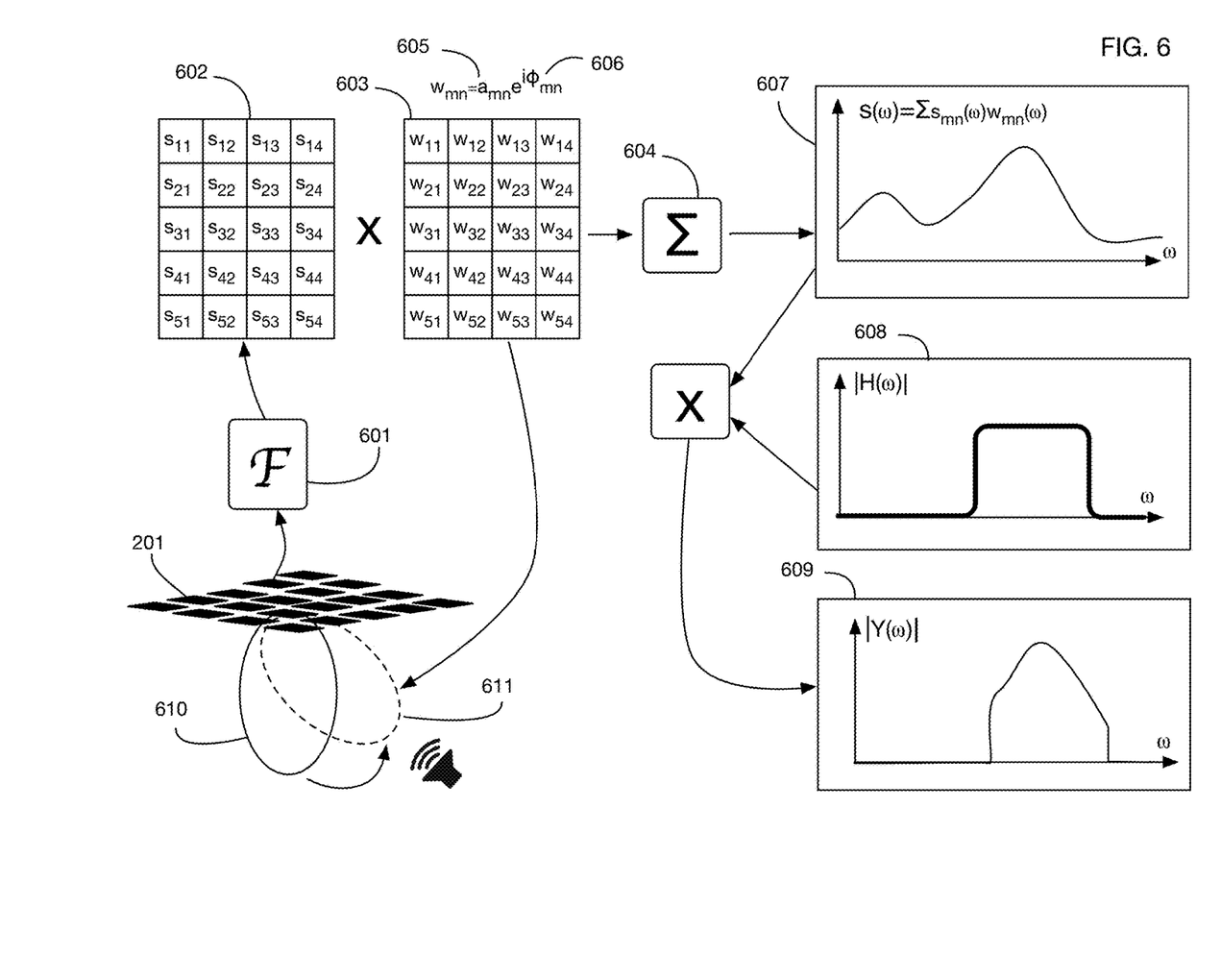
FIG. 6 illustrates an embodiment of the data analysis subsystem, which uses beamforming techniques to achieve directional reception of signals, and applies a band-pass filter to the result.

Processing layers or external processors may perform any type of data analysis on sensor data. FIG. 6 shows an illustrative data analysis performed by one or more embodiments. Sensor data received from sensor array 201 is transformed from the time domain to the frequency domain via Fourier transform 601. One or more embodiments may use any transform techniques, including for example, without limitation, continuous or discrete Fourier transform, FFT, z-transform, Laplace transform, or any integral transform with any kernel. One or more embodiments may perform data analysis in the time domain or space domain instead of or in addition to the frequency domain. In FIG. 6, the result of transform 601 is an array of frequency-domain signals 602. This array is weighted by an array of weighting factors or weighting functions 603, and the resulting product array is summed 604. Weighting factors 603 may in general be complex, with both an amplitude 605 and a phase 606. This general framework includes for example a class of beamforming techniques known in the art. These beamforming techniques may for example modify the directionality of a sensor array, to increase the gain of signals received from a specific direction or directions, and to attenuate the gain of signals received from other directions. For example, the weighting factor array 603 may be structured to rotate the main lobe of peak reception 610 for the sensor array to a different direction such as 611. One or more embodiments may use beamforming techniques to direct the receptivity of the sensor array in a particular direction, or to reject or attenuate data from certain directions. Beamforming techniques are known in the art; one or more embodiments may use any of these well-known techniques to process data from a sensor array.

The data analysis example shown in FIG. 6 further processes the signal 607 using a frequency-domain filter 608. The filter 608 shown is a band-pass filter; this is illustrative and one or more embodiments may use any desired filter, including for example, without limitation, a band-pass filter, a band-stop filter, a high-pass filter, a low-pass filter. A band-pass filter may be desirable, for example, when the data of interest falls within a known frequency range, and noise or undesired signals fall largely outside of this frequency range. The resulting output 609 may be further processed via additional algorithms or filters as desired.

Figure 7:
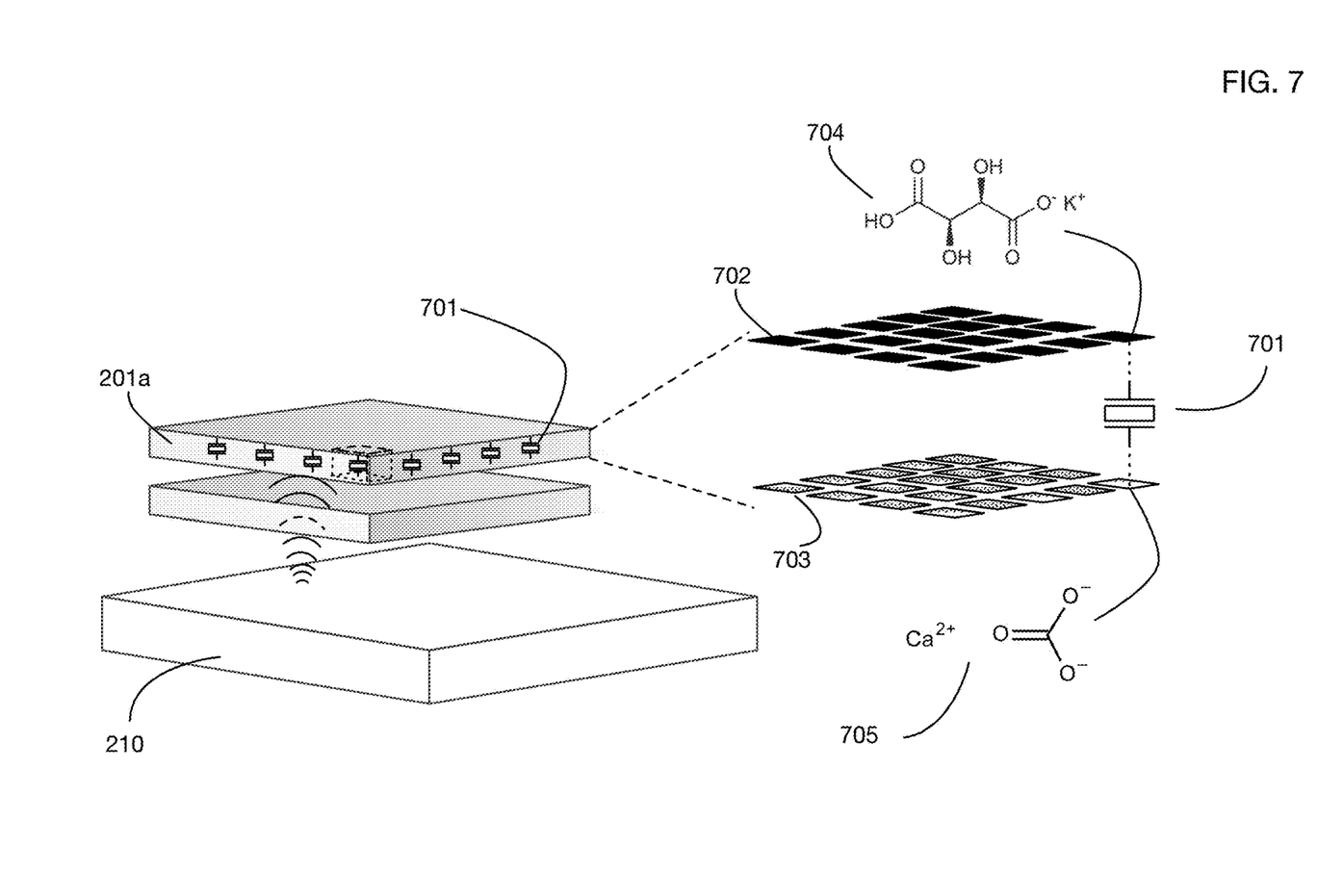
FIG. 7 illustrates an embodiment of the sensor array that uses piezoelectric acoustic sensors formed from adjacent layers of calcium carbonate and potassium bitartrate.

One or more embodiments may use sensor arrays of any type, to measure any desired property or properties of an object. One or more embodiments may use acoustic sensors to measure sound or vibration emitted from, reflected from, or transmitted through an object or a portion of an object. In particular, one or more embodiments may use piezoelectric acoustic sensors that transform pressure variations into electrical signals. FIG. 7 illustrates an embodiment with an array 201a of piezoelectric acoustic sensors, such as cell 701 in the array. In one or more embodiments, an array of piezoelectric acoustic sensors may be formed from a pair of adjacent layers with specific chemical compositions in the adjacent cells to generate a piezoelectric effect. In FIG. 7, array 201a is formed from adjacent layers 702 and 703. Cells of layer 702 contain potassium bitartrate 704 ($KC_4H_5O_6$); corresponding adjacent cells of layer 703 contain calcium carbonate 705 ($CaCO_3$). The interaction of the adjacent potassium bitartrate and calcium carbonate cells generates a piezoelectric sensor 701 in each cell of array 201a. This configuration is illustrative; one or more embodiments may use any layers of any chemical composition to form piezoelectric sensors or any other type of sensors.

Figure 8:
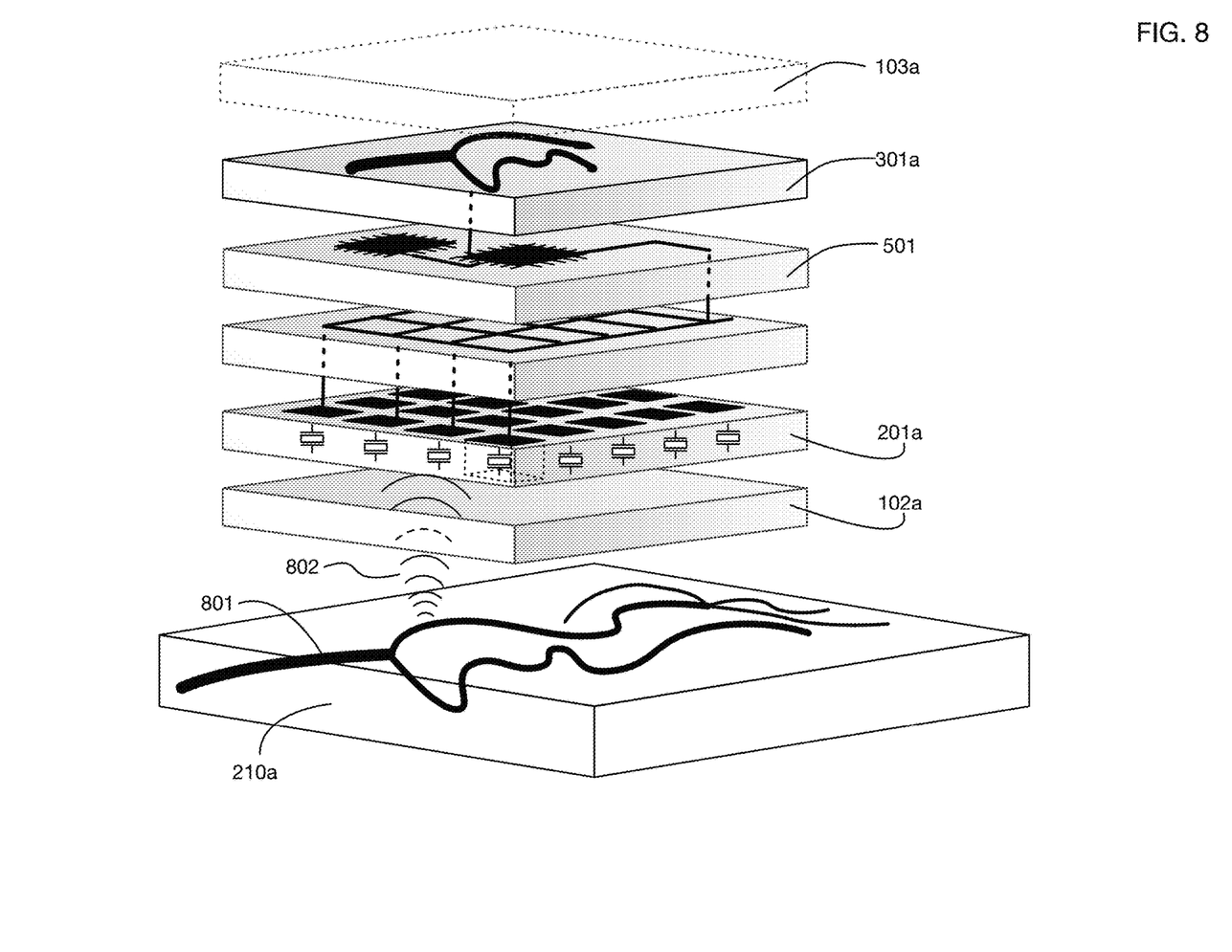
FIG. 8 illustrates an embodiment that uses a piezoelectric acoustic sensor array to measure blood flow, and displays the location of blood vessels on a display integrated into the fabric.

One or more embodiments of the fabric may be used to measure one or more biological properties of a human body. For example, one or more embodiments may use acoustic sensors to detect blood flow, and may use this information to map the location of blood vessels. A potential application for a blood vessel mapping fabric may be phlebotomy, for example: a phlebotomist may for instance attach a fabric with sensors to a patient's skin to visualize the underlying vessels prior to drawing blood. FIG. 8 illustrates an embodiment of the invention that measures the presence of blood vessels 801 in a portion 210a of a human body. The flow of blood through vessels 801 generates sounds 802 that are detected by array 201a of acoustic sensors. In the embodiment shown, processing is performed within the fabric in processor layer 501, and outputs are transmitted to display layer 301a. Data analysis performed by the processor layer may for example include beamforming to focus the sensor array to the region directly beneath the skin, or to another region of interest. Data analysis may also for example include frequency filtering to eliminate or attenuate sound signals outside the expected frequencies generated by the blood flow. One or more embodiments may perform processing or display external to the fabric. The pattern displayed on display layer 301a recreates the location of blood vessels 801 beneath the fabric. For a phlebotomy application, the outer cladding layer 103a may for example be a transparent, compliant, layer that can be easily pierced by a needle for a blood draw; the inner cladding 102a may for example contain an adhesive for attachment to a patient's skin.

Figure 9:
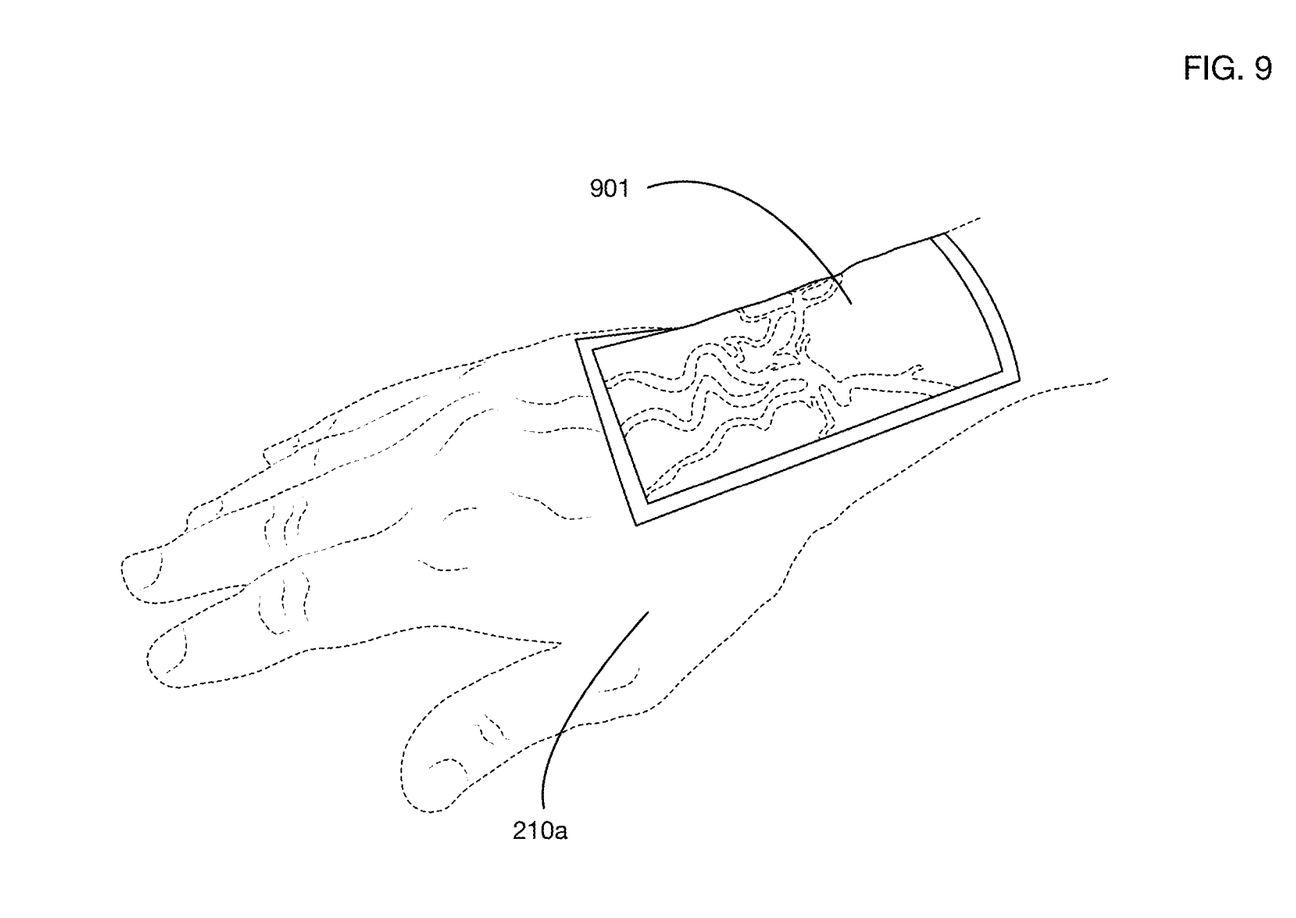
FIG. 9 shows a view of the embodiment of FIG. 8 placed on a hand.

FIG. 9 illustrates a diagram of the embodiment shown in FIG. 8, where the fabric 901 is attached to the hand 210a of a patient to visualize the underlying blood vessels.

Figure 10:
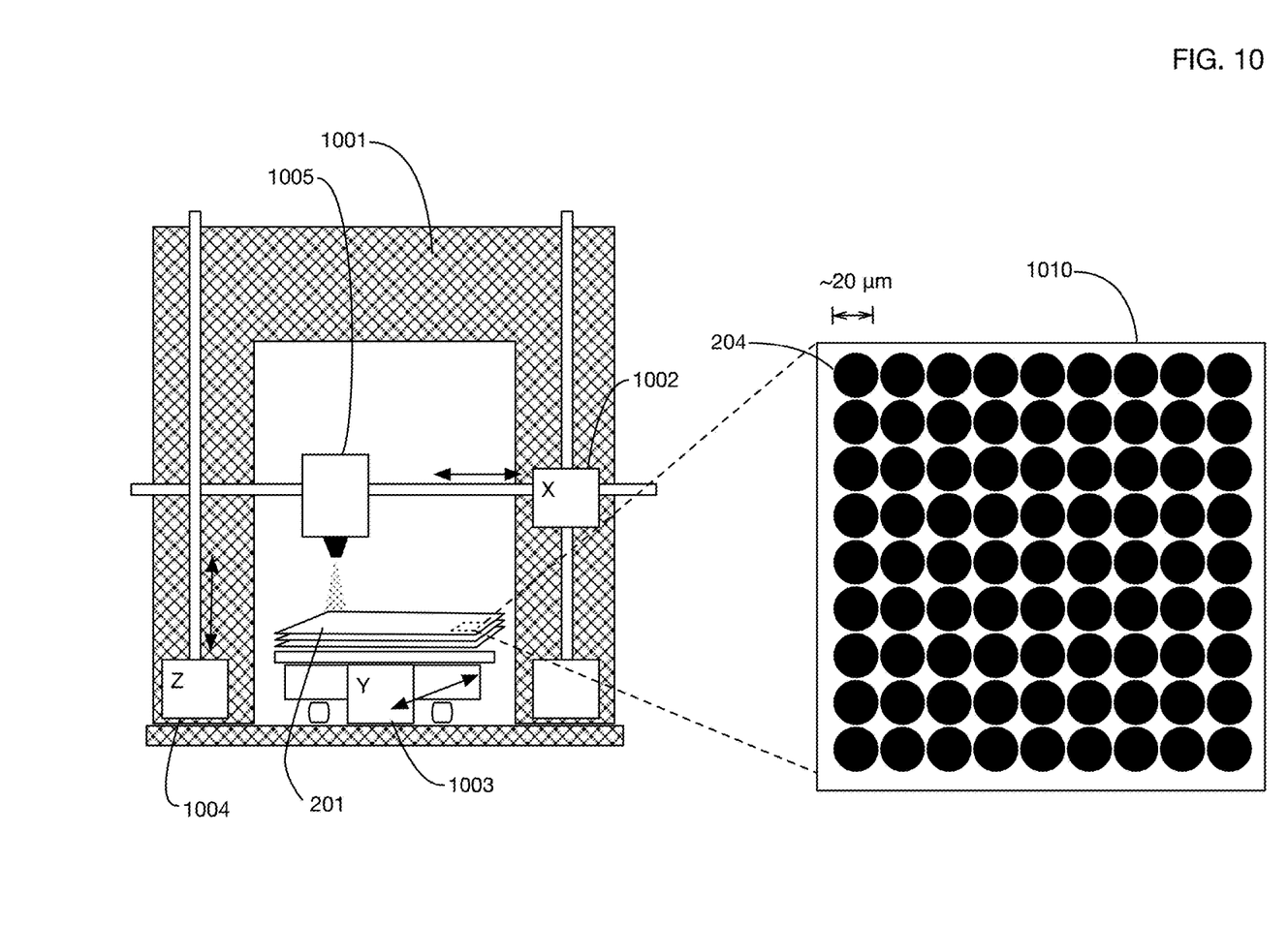
FIG. 10 illustrates a high-density sensor array constructed using a 3D printer.

One or more embodiments may use very small cells for sensor arrays, displays, processors, or other components embedded into the laminar layers. For example, one or more embodiments may use sensor cells with widths less than or equal to 300 micrometers. This illustrative cell width may for example provide sensor density of more than 1000 sensors per square centimeter of sheet surface area. This density is illustrative; one or more embodiments may use sensors of any size and density. Embodiments may have sheets of any desired size. For example, a sheet of 100 square centimeters in area may have more than 100,000 total sensors in the sheet's sensor array. Cell widths of 300 micrometers or less may be achieved for example using readily available 3D printing technologies, which can achieve resolution of less than 20 micrometers. FIG. 10 shows an illustrative process for generating high density sensor arrays. 3D printer 1001 includes three axis actuators 1002, 1003, and 1004, and a material deposition head 1005. The figure illustrates deposition of sensor material onto sensor array layer 201. Close up 1010 of a portion of layer 201 shows that cell widths may be for example 20 micrometers, a resolution that is readily achievable by current 3D printing technology.

While the invention herein disclosed has been described by means of specific embodiments and applications thereof, numerous modifications and variations could be made thereto by those skilled in the art without departing from the scope of the invention set forth in the claims.

What is claimed is:

1. A surface mountable sensor array fabric, comprising:
a sheet comprising one or more laminar layers, said sheet comprising a top side and a bottom side, wherein said bottom side of said sheet is configured to be placed on or proximate to a surface of an object;
a sensor array integrated into at least one of said one or more laminar layers, and comprising a plurality of sensors,
wherein each of said plurality of sensors generates sensor data that measures a property of said object; and,
wherein said plurality of sensors comprise piezoelectric acoustic sensors;
a communications array integrated into at least one of said one or more laminar layers,
wherein said communications array comprises an electrical connection to each of said plurality of sensors; and,
wherein said communications array obtains said sensor data from each of said plurality of sensors via said electrical connection;
a sensor data analysis subsystem coupled to said communications array, and comprising at least one processor,
wherein said sensor data analysis subsystem
receives said sensor data from said communications array; and,
analyzes said sensor data to form one or more outputs; and,
a display subsystem coupled to said sensor data analysis subsystem, and comprising at least one display, wherein said display subsystem
receives said one or more outputs from said sensor data analysis subsystem;
displays said one or more outputs on said at least one display;
wherein said sensor array is integrated into a first sensor layer and a second sensor layer adjacent to said first sensor layer, wherein
said first sensor layer comprises a first array of calcium carbonate cells comprising $CaCO_3$; and,
said second sensor layer comprises a second array of potassium bitartrate cells comprising $KC_4H_5O_6$;
wherein each potassium bitartrate cell in said second array of potassium bitartrate cells is aligned with a corresponding calcium carbonate cell in said first array of calcium carbonate cells.

2. The system of claim 1, wherein
said display subsystem is integrated into at least one of said one or more laminar layers; and,
said at least one display is visible to a viewer that views said top side of said sheet.

3. The system of claim 2, wherein said at least one display comprises a plurality of liquid crystal display pixels.

4. The system of claim 1, wherein
said object or a portion of said object comprises a grid of object regions;
said one or more outputs comprise a grid of output values in one to one correspondence with said grid of object regions; and,
said at least one display comprises a grid of display elements in one to one correspondence with said grid of output values;
wherein each display element in said grid of display elements displays a corresponding output value, which measures said property of a corresponding object region.

5. The system of claim 4, wherein
said display subsystem is integrated into at least one of said one or more laminar layers;
said at least one display is visible to a viewer that views said top side of said sheet; and,
when said sheet is placed on or proximate to said surface of said object,
each display element in said grid of display elements is located substantially above the corresponding object region along an axis perpendicular to said sheet and directed from said bottom side of said sheet to said top side of said sheet.

6. The system of claim 1, wherein
said sensor data analysis subsystem is integrated into at least one of said one or more laminar layers.

7. The system of claim 1, wherein
said at least one processor comprises one or more of a microprocessor, an array of microprocessors, a digital signal processor, an array of digital signal processors, an analog filter circuit, an array of analog filter circuits, a computer, a laptop computer, a tablet computer, a desktop computer, a server computer, a network of computers, a mobile device, and a network of mobile devices.

8. The system of claim 1, wherein said analyzes said sensor data to form one or more outputs comprises application of beamforming signal processing to said sensor data in order to amplify signals arriving from a first set of directions and to attenuate signals arriving from a second set of directions.

9. The system of claim 1, wherein said analyzes said sensor data to form one or more outputs comprises application of one or more of a band-pass filter, a band-stop filter, a high-pass filter and a low-pass filter to said sensor data.

10. The system of claim 1, wherein
said plurality of sensors comprises at least 100 sensors.
11. The system of claim 1, wherein
said plurality of sensors comprises at least 1000 sensors.
12. The system of claim 1, wherein
said plurality of sensors comprises a number of sensors greater than or equal to 10 multiplied by an area of said sheet in square centimeters.
13. The system of claim 1, wherein
said plurality of sensors comprises a number of sensors greater than or equal to 1000 multiplied by an area of said sheet in square centimeters.
14. The system of claim 1, wherein said one or more laminar layers comprise
an inner cladding layer on said bottom side of said sheet; and,
an outer cladding layer on said top side of said sheet.
15. The system of claim 1, wherein
said object is a person;
said plurality of sensors measure one or more biological properties of one or more body parts of said person; and,
said one or more biological properties comprise one or more of
sound;
pressure;
temperature;
sweat rate;
electrical resistance;
electrical conductivity;
electrical voltage;
electrical current;
electromagnetic field;
motion;
orientation;
fluid flow;
strain;
pH;
tissue type;
tissue composition;
cell type; and,
chemical composition.
16. The system of claim 5, wherein
said plurality of sensors comprise acoustic sensors;
said object is a person; and,
said property of said object is presence or size of a blood vessel indicated by a sound of blood flow through said blood vessel.
17. A surface mountable sensor array fabric, comprising:
a sheet comprising one or more laminar layers, said sheet comprising a top side and a bottom side, wherein said bottom side of said sheet is configured to be placed on or proximate to a surface of an object;
an inner cladding layer on said bottom side of said sheet;
a sensor array integrated into at least one of said one or more laminar layers, and comprising a plurality of sensors,
wherein each of said plurality of sensors generates sensor data that measures a property of said object; and,
wherein said plurality of sensors comprise piezoelectric acoustic sensors;
a communications array integrated into at least one of said one or more laminar layers,
wherein said communications array comprises an electrical connection to each of said plurality of sensors; and,
wherein said communications array obtains said sensor data from each of said plurality of sensors via said electrical connection;
a sensor data analysis subsystem coupled to said communications array, and comprising at least one processor,
wherein said sensor data analysis subsystem
receives said sensor data from said communications array; and,
analyzes said sensor data to form one or more outputs via application of beamforming signal processing to said sensor data in order to amplify signals arriving from a first set of directions and to attenuate signals arriving from a second set of directions;
a display subsystem integrated into at least one of said one or more laminar layers, comprising an array of display pixels, wherein
said display subsystem receives said one or more outputs from said sensor data analysis subsystem;
said display subsystem displays said one or more outputs on said array of display pixels; and,
said array of display pixels is visible to a viewer that views said top side of said sheet; and,
an outer cladding layer on said top side of said sheet;
wherein said sensor array is integrated into a first sensor layer and a second sensor layer adjacent to said first sensor layer, wherein
said first sensor layer comprises a first array of calcium carbonate cells comprising $CaCO_3$; and,
said second sensor layer comprises a second array of potassium bitartrate cells comprising $KC_4H_5O_6$;
wherein each potassium bitartrate cell in said second array of potassium bitartrate cells is aligned with a corresponding calcium carbonate cell in said first array of calcium carbonate cells.

* * * * *